US012071398B2

(12) United States Patent
Checinski et al.

(10) Patent No.: US 12,071,398 B2
(45) Date of Patent: Aug. 27, 2024

(54) PROCESS FOR PRODUCING METHANOL

(71) Applicant: CreativeQuantum GmbH, Berlin (DE)

(72) Inventors: Marek Pawel Checinski, Berlin (DE); Matthias Beller, Ostseebad Nienhagen (DE); Pavel Ryabchuk, Wezembeek-Oppem (BE); Kathrin Junge, Rostock (DE)

(73) Assignee: CREATIVEQUANTUM GMBH, Berlin (DE)

( * ) Notice: Subject to any disclaimer, the term of this patent is extended or adjusted under 35 U.S.C. 154(b) by 582 days.

(21) Appl. No.: 17/418,262

(22) PCT Filed: Dec. 10, 2019

(86) PCT No.: PCT/EP2019/084355
§ 371 (c)(1),
(2) Date: Jun. 25, 2021

(87) PCT Pub. No.: WO2020/136003
PCT Pub. Date: Jul. 2, 2020

(65) Prior Publication Data
US 2022/0048839 A1   Feb. 17, 2022

(30) Foreign Application Priority Data
Dec. 28, 2018  (DE) .................... 10 2018 133 689.6

(51) Int. Cl.
*C07C 29/156* (2006.01)
*B01J 31/18* (2006.01)

(52) U.S. Cl.
CPC ........... *C07C 29/156* (2013.01); *B01J 31/183* (2013.01); *B01J 31/189* (2013.01); *B01J 2231/62* (2013.01); *B01J 2531/64* (2013.01); *B01J 2531/72* (2013.01); *B01J 2531/842* (2013.01)

(58) Field of Classification Search
CPC ... C07C 29/256; C07C 31/04; C07C 2523/34; B01J 31/183; B01J 31/189; B01J 2231/62; B01J 2531/72; B01J 2531/842
See application file for complete search history.

(56) References Cited

U.S. PATENT DOCUMENTS 4,421,863 A * 12/1983 Duranleau ............ C07C 29/158
518/701
10,385,084 B2   8/2019 Morris et al.

2003/0158270 A1   8/2003 Mahajan
2010/0324332 A1  12/2010 Carrington-Smith et al.
2016/0060195 A1   3/2016 Ding et al.

FOREIGN PATENT DOCUMENTS

EP    0075937 B1    4/1983
JP    S58131926 A   8/1983
JP    S61204144 A   9/1986
JP    H1059884 A    3/1998

OTHER PUBLICATIONS

Saravanakumar Elangovan, et al., "Selective Catalytic Hydrogenations of Nitriles, Ketones, and Aldehydes by Well-Defined Manganese Pincer Complexes", Journal of the American Chemical Society, May 24, 2016, pp. 8809-8814, vol. 138, ACS Publications, Washington D.C., USA.
D. Mahajan, "Atom-economical reduction of carbon monoxide to methanol catalyzed by soluble transition metal complexes at low temperatures", Topics in Catalysis, Mar. 2005, pp. 209-214, vol. 32, Nos. 3-4, Springer, Berlin, Germany, XP019292182.
Simona Mazza, et al., "Chemoselective Hydrogenation and Transfer Hydrogenation of Aldehydes Catalyzed by Iron(II) PONOP Pincer Complexes", Organometallics, Apr. 8, 2015, pp. 1538-1545, vol. 34, ACS Publications, Washington D.C., USA.
Iwao Omae, "Carbon Dioxide Utilization by the Five-Membered Ring Products of Cyclometalation Reactions", Current Organic Chemistry, Dec. 2016, pp. 953-962, vol. 20, Bentham Science Publishers, Sharjah, United Arab Emirates.
Pavel Ryabchuk, et al., "Molecularly Defined Manganese Catalyst for Low-Temperature Hydrogenation of Carbon Monoxide to Methanol", Journal of the American Chemical Society, Oct. 2, 2019, pp. 16923-16929, vol. 141, ACS Publications, Washington D.C., USA, XP055671522.
Sayan Kar, et al., "Manganese-Catalyzed Sequential Hydrogenation of $CO_2$ to Methanol via Formamide", ACS Catalysis, Aug. 23, 2017, pp. 6347-6351, vol. 7, ACS Publications, Washington D.C., USA, XP055671581.
Sayan Kar, et al., "Catalytic Homogeneous Hydrogenation of CO to Methanol via Formamide", Journal of the American Chemical Society, Aug. 5, 2019, pp. 12518-12521, vol. 141, ACS Publications, Washington D.C., USA, XP055671536.
Garbe, Marcel et al.; "Homogeneous Catalysis by Manganese-Based Pincer Complexes"; European Journal of Organic Chemistry; Jun. 26, 2017; pp. 4344-4362; vol. 2017; No. 30; XP055671543; Wiley-VCH Verlag Gmbh & Co. KG; Weinheim, Germany.

* cited by examiner

*Primary Examiner* — Jafar F Parsa
(74) *Attorney, Agent, or Firm* — LEYDIG, VOIT & MAYER, LTD.

(57) ABSTRACT

A process for catalyzed reaction of CO and $H_2$ into methanol includes the step of reacting the CO and $H_2$ with a catalyst comprising a transition metal and at least one Lewis basic ligand together with at least one nucleophilic promoter so as to produce the methanol as a product.

20 Claims, No Drawings

PROCESS FOR PRODUCING METHANOL

CROSS-REFERENCE TO PRIOR APPLICATIONS

This application is a U.S. National Phase application under 35 U.S.C. § 371 of International Application No. PCT/EP2019/084355, filed Dec. 10, 2019, and claims benefit to German Patent Application No. DE 10 2018 133 689.6, filed Dec. 28, 2018. The International Application was published in English on Jul. 2, 2020 as WO 2020/136003 under PCT Article 21(2).

FIELD

The present invention concerns a process for the catalyzed reaction of CO and $H_2$ with a catalytic complex containing a transition metal as a central ion and at least one Lewis basic ligand together with a nucleophile promoter to the product methanol.

BACKGROUND

Methanol is a chemical with the formula $CH_3OH$ (a methyl group linked to a hydroxyl group, often-abbreviated MeOH). It is a key component of the chemical industry. Not only it can be used as a fuel component, but also as a basic building block in chemical industries with a production volume of >100 million metric tons in 2018.

SUMMARY

The invention is, therefore, based on the task of providing a process for the production of methanol, the energy requirement of which is significantly lower than that of the process known from the state of the art.

This task is solved by a procedure with the characteristics as disclosed herein.

Such a process converts CO and $H_2$ from a catalytic complex having a transition metal as central ion and a Lewis base ligand. The reaction also takes place in the presence of a nucleophile promoter.

In some aspects, disclosed is a process for catalyzed reaction of CO and $H_2$ into methanol, the process comprising reacting a catalyst comprising a transition metal as a central ion and at least one Lewis basic ligand together with at least one nucleophilic promoter, thereby producing the methanol.

DETAILED DESCRIPTION

In this invention, a conceptually novel approach to the hydrogenation of carbon monoxide is disclosed. This process involves the capture of CO and transformation of CO by a promoter under a $H_2$ containing atmosphere into a formamide or methyl formate and subsequent hydrogenation of the resulting intermediate in one process step i.e. to methanol. CO fixation can be achieved with various nucleophilic promoters like amines and nitrogen heterocycles. As for hydrogenolysis of the amides or methyl formate it can be promoted with Mn, Fe, and Ru.

The potential reaction path is described as following:

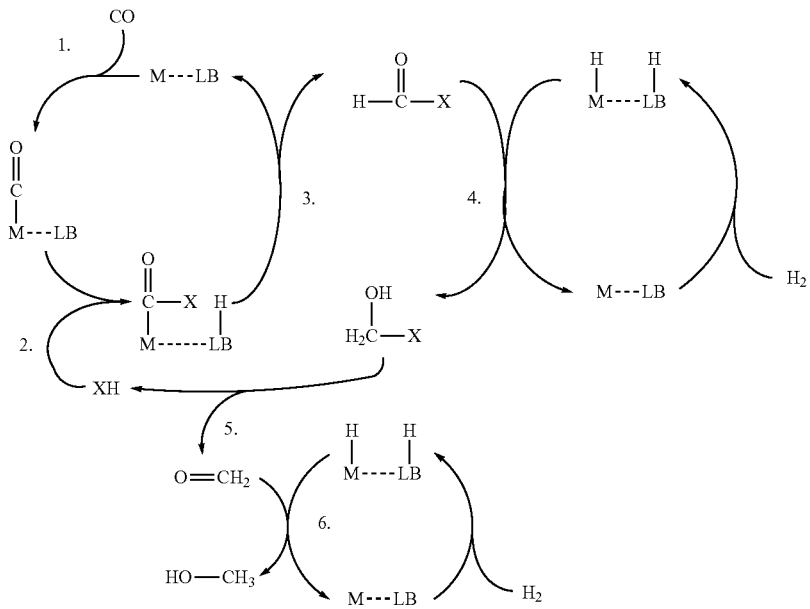

FIG. 1 Reaction scheme for a reaction according to the invention

A disadvantage in all known reaction mechanisms, however, is that the reaction must be carried out under relatively harsh conditions, especially above 250° C. and high pressures of over 100 bar. This makes current processes very energy intense, which is problematic from both an economic and environmental point of view. By reducing energy consumption, opex and carpex can reduce costs and improve the sustainability of the process.

1. CO addition to the metal-ion
2. Lewis base assisted X—H bond split of the promoter and addition to CO followed by an elimination of the carbonylated H—X as H—CO—X
3. Elimination of H—CO—X
4. Hydrogenation of H—CO—X by the catalyst
5. Elimination of formaldehyde
6. Hydrogentation of formaldehyde to methanol In this reaction path the active center of the catalyst M-LB and the promoter X—H is crucial for the reaction.

The key discovery which enables the methanol synthesis was to find an appropriate catalyst and promoter combination, which would be compatible with CO and produce methanol under an $H_2$ containing atmosphere. Thus, in the initial stage of this study the effectiveness of various transition metal Lewis basic ligand complexes to cleave amides to amine and methanol, or esters to alcohole with $H_2$/CO mixtures was investigated.

It is essential for the invention that the whole reaction takes part with one mixture and does not require temporally and/or locally separated steps.

Moreover, the process can be performed as a batch process or as a continuous process.

It is possible to have additional compound in the reaction mixture, particularly $CO_2$. This enables the use of synthesis gas from different sources, like reverse water-gas shift reaction, without any cleaning steps.

The catalyst is a metal catalyst with the lead structure M-LB, where M is a metal ion and LB is the center of the at least one Lewis base. In its simplest form the catalyst can be described as $M_xN_y$ (x=1-4, y=1-2) which is depicted in FIG. 2:

FIG. 2

In this easiest form the catalyst is typically a solid compound without any ligand.

However, also metal organic complexes as shown in FIG. 3 are possible, whereby M is a metal ion and LB is the center of the at least one Lewis base. R is at least one ligand comprising at least one atom selected from a group comprising N, P, O or S. In this variant, LB contains least one atom selected from a group comprising N, P, O, S or C, independent from the atom of the ligand. R and LB can be linked for example by a C2 (—C2H4-) or C3 (—C3H6-) chain. Chelating ligands are particularly preferred. According to this scheme (FIG. 3) the ligand could also be ortho-Aminoaniline.

FIG. 3

FIG. 4 shows another metal organic complexes with two different ligands. According to this scheme, the ligand could also be for example an ortho-Aminoaniline derivative with a third chelating rest.

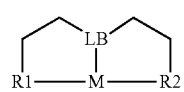

FIG. 4

Particularly preferred is a system with a metal ion selected from the group Mn, Fe, Cr, Mo, W, Re, Co, Rh, Ir, Ni and Pd a Lewis base containing at least one nitrogen atom and R, R1 and/or R2 containing each at least one phosphor, nitrogen or sulfur atom.

The ligand can be a pincer type complex. It can be selected from the pincer type group of PNP, where R1=P(iPr)$_2$, R2=P(iPr)$_2$, and LB=NH. Other pincer types would be PNN, NNN, NNS or NNC, where P can be P=PPh$_2$, PEt$_2$ and N can be N=NH$_2$, NEt$_2$, Pyridine, Pyrrole, Indole, Isoindole, Imidazol, Benzimidazol, Aniline and S can be S=SMe, SEt, SPh.

The transition metal is an ion selected from the group consisting of manganese, iron, molybdenum, chromium, cobalt, ruthenium rhodium, nickel or palladium, in which manganese, iron, or molybdenum in particular exhibit good capabilities. In particular, the use of manganese as a central ion shows high turnover rates (TON).

It is also preferred that the procedure takes place in the presence of a base, which further enables a stabilization of the coordination at the central ion and/or deprotonation. In particular, it has been found that hydroxide and/or the alkali oxide of at least one of the elements Lithium, Sodium, Potassium or Calcium can be used.

It was found that the promoter plays an important role in the CO hydrogenation process. In particular, promoters such as primary, secondary amines, primary anilines, and nitrogen heterocycles: pyrroles, indoles, imidazoles, carbazoles, benzimidazoles have been found active.

Promoters that show TON higher than 50, are of particular interest, since they indicate that the amount of methanol produced exceeds the amount nitrogen-promoter. The most efficient promoters are secondary anilines, pyrroles, indoles and carbazoles.

In principle, the following promoters were tested successfully:

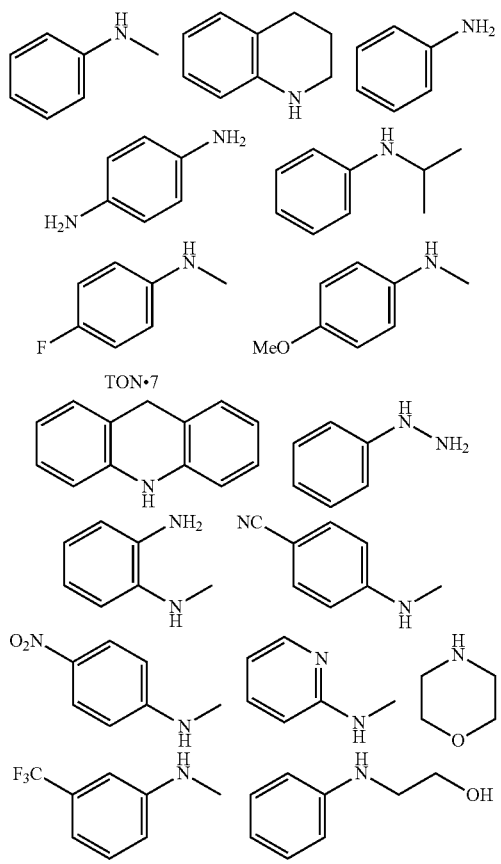

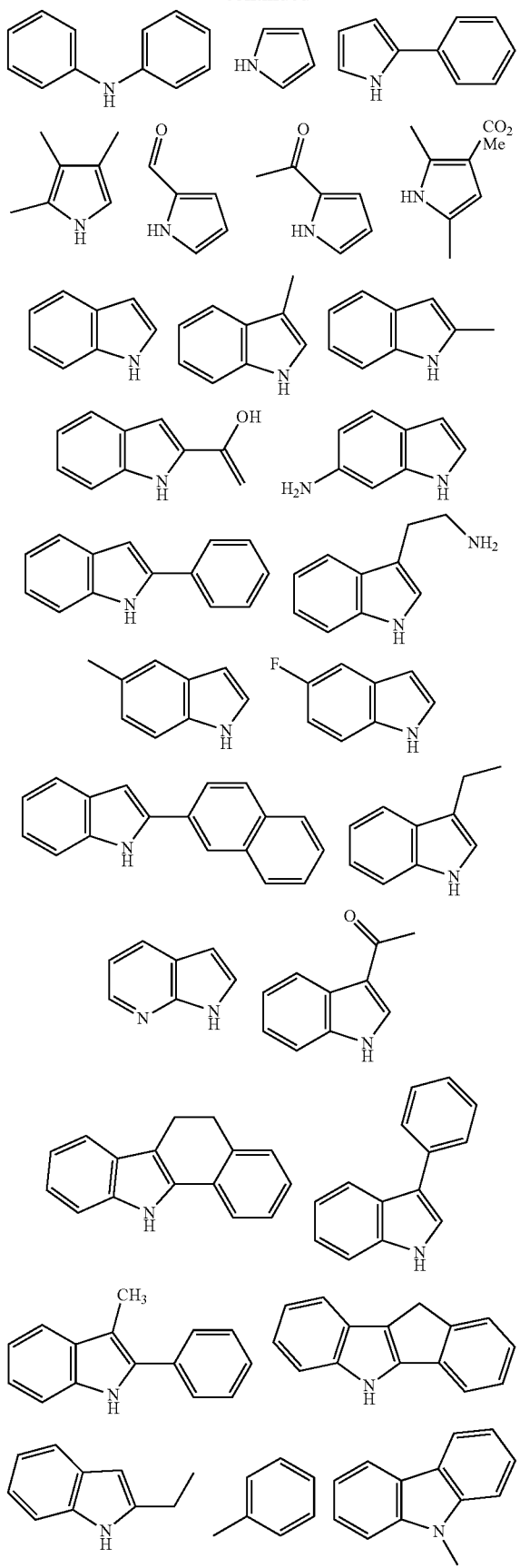
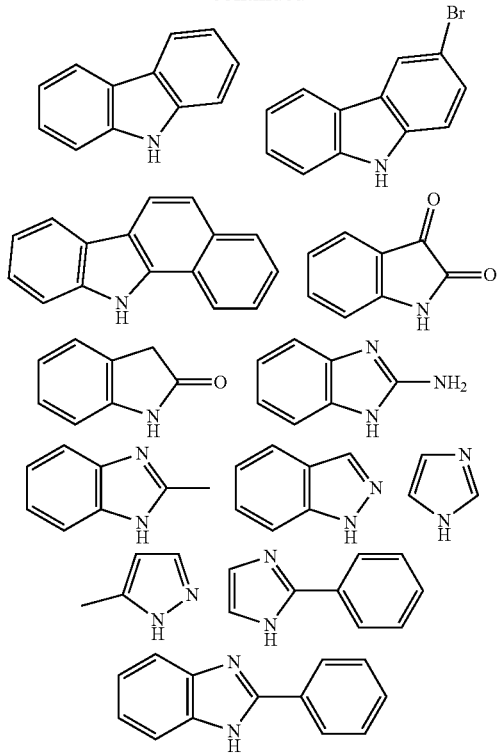

It has also been shown that a ratio r1 between promoter and base between 1:1 and 3:1 and/or a ratio r2 between base and catalyst between 25:1 and 100:1 is particularly favorable. The highest turnover rates were found here.

In addition, it has proved to be particularly advantageous to carry out the process at a temperature below 160° C. The temperature of the sample is therefore below 160° C. This allows further energy savings.

It is advantageous that the reaction takes place in weak coordinating (to the catalyst) or a non-polar solvent. Cyclohexane is particularly preferred here. This reliably prevents interactions with the active center of the catalyst.

CO and $H_2$ are both introduced into the process preferably at a partial pressure between 0.1 and 50 bar. CO with a pressure between 0.1 and 25 bar, hydrogen with a pressure between 30 and 50 bar is introduced into the system in particular. Increasing the pressure of the hydrogen slightly above that of the CO ensures that the downstream hydrogenation actually takes place as completely as possible. For CO it is not necessary to increase those pressures further.

Furthermore, it is possible to carry out the reaction homogeneously catalyzed. The advantage of a homogeneous catalyzed reaction is that there are no additional material transport effects such as adsorption, desorption on surfaces or additional restrictions due to a limited surface area.

At the same time, however, it is also conceivable to stabilize the complex according to the invention on a surface and to apply a heterogeneously catalyzed reduction. The advantages of the reaction would be on the one hand that it corresponds to the processes used in the chemical industry, so that only the catalyst has to be replaced and the operating conditions changed, and on the other hand hydrogen catalyzed processes usually facilitate the separation of the catalyst.

Methanol production from CO and H2 at a pressure between 10 and 40 bar is therefore particularly preferred, with the pressure of each component being independent of that of the others. The temperature lies between 120 and 150° C. The catalyst is present in a concentration between 1 and 10 mmol. A manganese-PNP complex is used as catalyst. In addition, 0.2 to 1 mmol aniline are used as promoters or 0.1 to 0.5 mmol are used as base. The entire reaction is performed in cyclohexane.

EXAMPLES

The following examples show individual aspects of the invention. All the features described and/or depicted, either individually or in any combination, constitute the subject matter of the application, irrespective of whether they are depicted in the claims or referred back to them.

Further Identified Catalysts

According to the identified reaction path, other catalysts could be identified by quantum mechanical virtual high throughput screenings. The most important steps of the reaction are the free energy of the addition of the promoter to the carbonyl complex (Scheme step 2) and the free energy transition barrier (TS) of the elimination of the formamide (Scheme step 3).

Mn-1
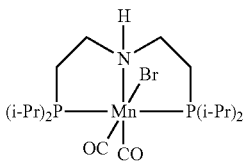

Mn-2
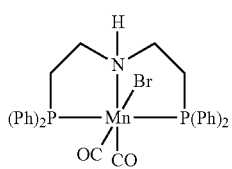

Mn-3
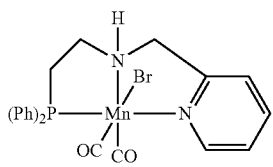

Mn-4
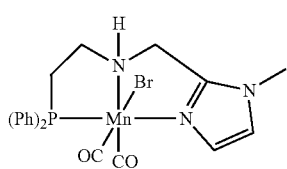

Fe-5
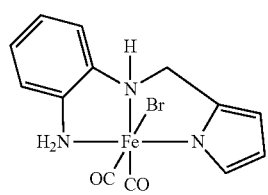

Fe-6
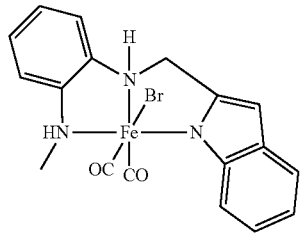

| Promoter | Catalyst | Step 2 - dG° [kJ/mol] | TS Step 3 - dG°,‡ [kJ/mol] |
| --- | --- | --- | --- |
| Aniline | Mn-1 | −34 | 176 |
| Pyrrole | Mn-1 | −2 | 150 |
| Pyrrole | Mn-2 | −8 | 156 |
| Pyrrole | Mn-3 | 8 | 113 |
| Pyrrole | Mn-4 | 8 | 125 |
| Aniline | Mn-3 | −27 | 142 |
| 3-Me-Indole | Mn-3 | 1 | 112 |
| Aniline | Fe-5 | −30 | 120 |
| Aniline | Fe-6 | −29 | 120 |

General Procedure for the Hydrogenation of Amides with Manganese Complexes Using CO/H$_2$ A flame-dried 8 mL vial with a magnetic stir bar was charged with 5 μmmol of Mn-1, 0.25 mmol of amide and 2 mL of dry solvent. The vial was capped with a septum and the mixture was stirred for 10 seconds. Then the reaction mixture was purged with Ar for 30 seconds and 0.125 mmol of base (t-BuOK) was added. The septum was punctured with a needle and the vial was placed in a 300 mL autoclave. The autoclave was purged with carbon monoxide 5 times (5-7 atm) and then pressurized to 5-20 atm. The autoclave was connected to a hydrogen line and was filled to 50 atm overall pressure. The autoclave was placed in a preheated aluminum block and stirred at 700 rpm at 150° C. for 20 h. Then the reaction was placed in ice, cooled and depressurized. The reaction vial was analyzed via GC and NMR analysis, amount of methanol and corresponding amine was determined via GC using n-hexadecane as a standard.

General Procedure for the Conversion of CO/H$_2$ to Methanol

A flame-dried 8 mL vial with a magnetic stir bar was charged with 5 μmmol of Mn-1, 0.25-6.0 mmol of promoter and 2 mL of dry solvent. The vial was capped with a septum and the mixture was stirred for 10 seconds. Then the reaction mixture was purged with Ar for 30 seconds and 0.125 mmol of base (t-BuOK) was added. The septum was punctured with a needle and the vial was placed in a 300 mL autoclave. The autoclave was purged with carbon monoxide 5 times (5-7 atm) and then pressurized to 20 atm. The autoclave was connected to a hydrogen line and was filled to 50 atm overall pressure. The autoclave was placed in a preheated aluminum block and stirred at 700 rpm at 150° C. for 20 h. Then the reaction was placed in ice, cooled and depressurized. The reaction vial was analyzed via GC and NMR analysis, the amount of methanol was determined via GC using n-hexadecane as a standard.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A process for catalyzed reaction of CO and $H_2$ into methanol, the process comprising:
   reacting the CO and $H_2$ with a catalyst comprising a transition metal and at least one Lewis basic ligand together with at least one nucleophilic promoter so as to produce the methanol as a product;
   wherein the catalyst is a metal organic complex with at least one ligand comprising N, P. O. or S;
   wherein the ligand is a pincer type complex;
   wherein the transition metal is a central ion; and
   wherein the central ion comprises Mn, Re. Fe. Cr. W. Ru, Co, Rh, Ir, Pd or Mo.

2. The process according to claim 1, wherein the catalyst comprises at least one of the following complexes:

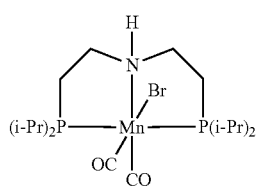
Mn-1

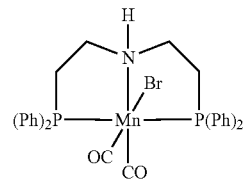
Mn-2

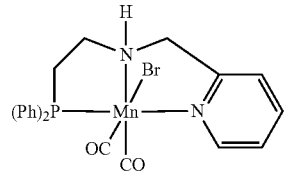
Mn-3

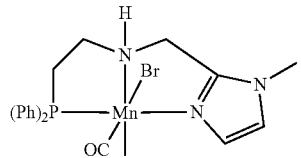
Mn-4

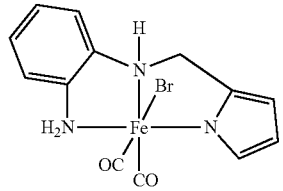
Fe-5

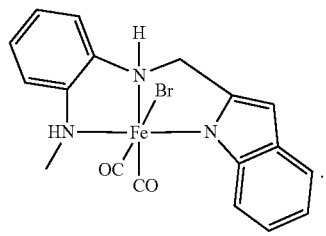
Fe-6

3. The process according to claim 1, wherein the process takes place in presence of a base.

4. The process according to claim 3, wherein the base is a hydroxide and/or an alkoxide of at least one of lithium, sodium, potassium or calcium.

5. The process according to claim 1, wherein the at least one nucleophilic promoter comprises nitrogen or oxygen.

6. The process according to claim 1, wherein the at least one nucleophilic promoter comprises at least one N—H- Group.

7. The process according to claim 1, wherein the at least one nucleophilic promoter comprises at least one of the following compounds:

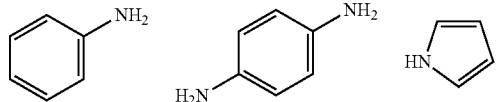

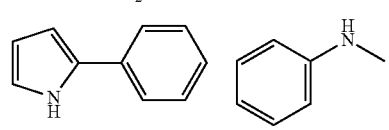

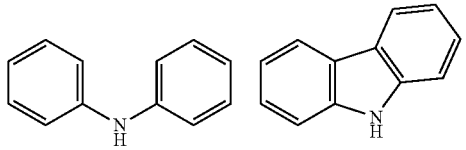

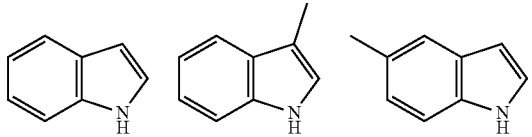

-continued

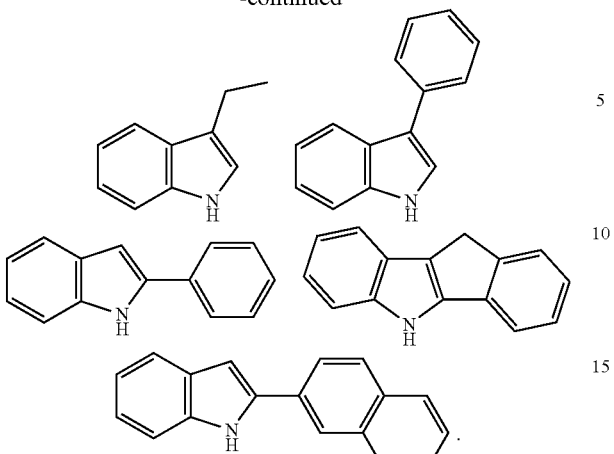

8. The process according to claim 3, wherein a ratio r1 between at least one nucleophilic promoter and the base is between 1:1 and 3:1 and/or a ratio r2 between the base and the catalyst is between 25:1 and 100:1.

9. The process according to claim 1, wherein the process is run at a temperature below 200° C.

10. The process according to claim 1, wherein the process takes place in a non-polar solvent.

11. The process according to claim 1, wherein all compounds are introduced with a partial pressure between 0.1 and 40 bar.

12. The process according to claim 1, wherein methanol is produced out of the CO and $H_2$ with a pressure between 0.1 and 40 bar independently from each other at a temperature between 120 and 150° C. in the presence of 1 to 10 µmol of a Mn-PNP complex, 0.2-1 mmol Aniline and 0.1 to 0.5 tBuOK in cyclohexane.

13. The process according to claim 6, wherein the at least one N—H-Group is a primary amine, a secondary amine, a primary aniline, or a nitrogen heterocycle.

14. The process according to claim 13, wherein the at least one N—H-Group is the nitrogen heterocycle, and the nitrogen heterocycle is a pyrrole, an indole, an imidazole, a carbazole, or a benzimidazole.

15. The process according to claim 10, wherein the non-polar solvent comprises cyclohexane.

16. The process according to claim 1, wherein a ratio r1 between at least one nucleophilic promoter and the Lewis basic ligand is between 1:1 and 3:1 and/or a ratio r2 between the Lewis basic ligand and the catalyst is between 25:1 and 100:1.

17. The process according to claim 1, wherein the pincer type complex comprises a PNP, PNN, NNN, NNS, or NNC pincer type complex.

18. The process according to claim 17, wherein P comprises $PPh_2$ or $PEt_2$, and wherein N comprises $NH_2$, $NEt_2$, pyridine, pyrrole, indole, isoindole, imidazole, benzimidazole, or aniline.

19. The process according to claim 17, wherein the pincer type complex comprises NNS, wherein N comprises $NH_2$, $NEt_2$, pyridine, pyrrole, indole, isoindole, imidazole, benzimidazole, or aniline, and wherein S comprises SMe, SEt, or SPh.

20. The process according to claim 1, wherein the nucleophilic promoter comprises at least one of the following compounds:

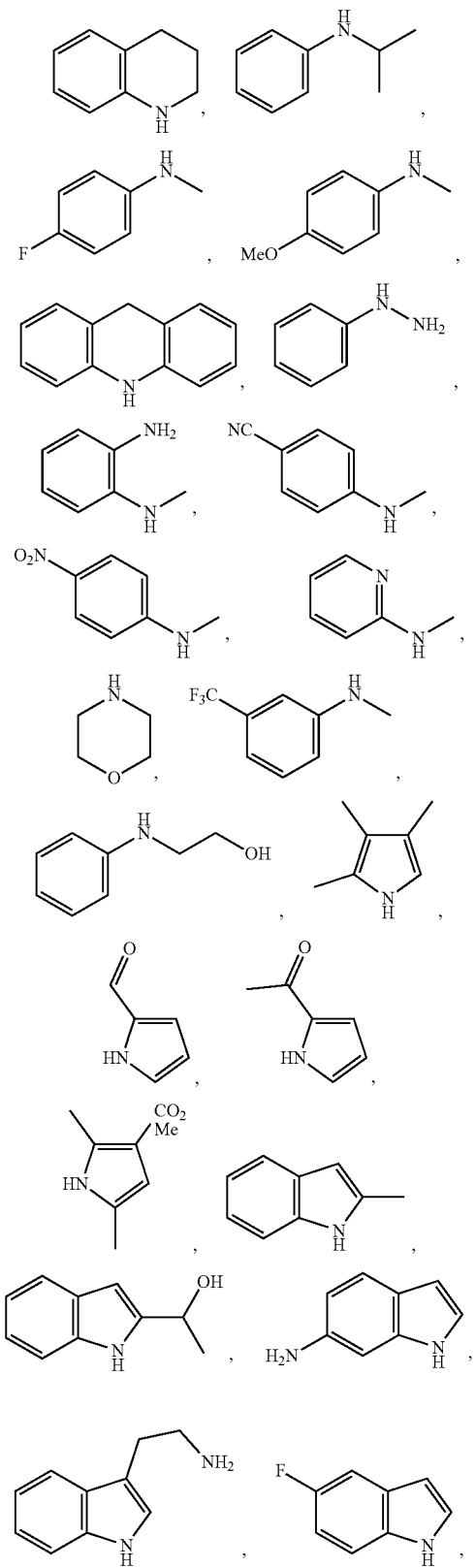

-continued
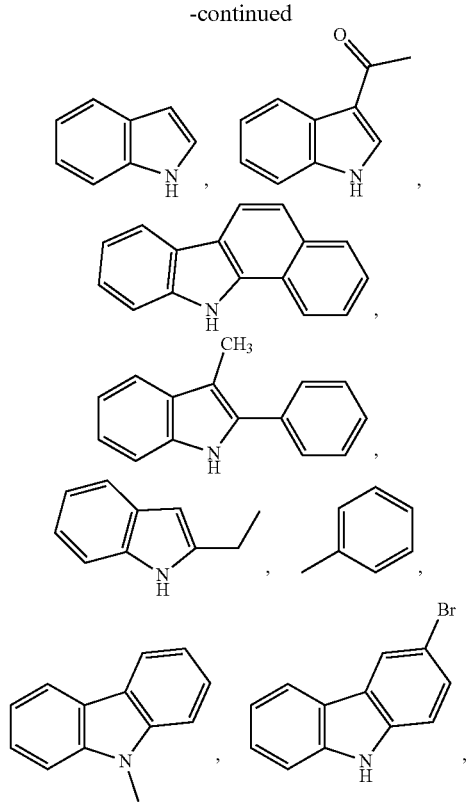
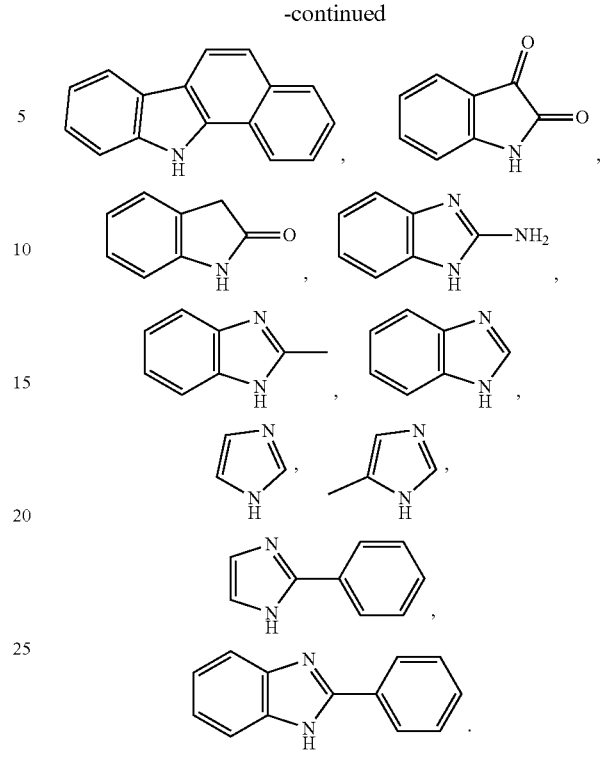
* * * * *